United States Patent
Ginsburg

(10) Patent No.: US 7,311,724 B1
(45) Date of Patent: Dec. 25, 2007

(54) METHOD FOR CONTROLLING A PATIENT'S BODY TEMPERATURE

(75) Inventor: Robert Ginsburg, Greenwood Village, CO (US)

(73) Assignee: Radiant Medical, Inc., Redwood City, CA (US)

( * ) Notice: Subject to any disclaimer, the term of this patent is extended or adjusted under 35 U.S.C. 154(b) by 0 days.

(21) Appl. No.: 10/292,978

(22) Filed: Nov. 12, 2002

Related U.S. Application Data

(60) Continuation of application No. 09/943,552, filed on Aug. 30, 2001, now Pat. No. 6,656,209, which is a continuation of application No. 09/130,852, filed on Aug. 7, 1998, now Pat. No. 6,306,161, which is a division of application No. 09/100,275, filed on Jun. 19, 1998, now Pat. No. 6,110,168, which is a continuation-in-part of application No. 08/584,013, filed on Jan. 8, 1996, now Pat. No. 5,837,003, which is a continuation-in-part of application No. 08/324,853, filed on Oct. 18, 1994, now Pat. No. 5,486,208, which is a continuation of application No. 08/015,774, filed on Feb. 10, 1993, now abandoned.

(51) Int. Cl.
*A61F 7/12* (2006.01)
(52) U.S. Cl. .................................................. 607/105
(58) Field of Classification Search .............. 607/96, 607/108–112, 114, 113, 105, 106
See application file for complete search history.

(56) References Cited

U.S. PATENT DOCUMENTS

| | | | |
|---|---|---|---|
| 2,308,484 A | 1/1943 | Auzin et al. | 604/103 |
| 3,425,419 A | 2/1969 | Dato | 607/113 |
| 3,726,283 A | 4/1973 | Dye et al. | 604/247 |
| 3,788,328 A | 1/1974 | Alley et al. | 604/178 |
| 3,995,617 A | 12/1976 | Watkins et al. | 604/247 |
| 4,014,317 A | 3/1977 | Bruno | 604/247 |
| 4,038,519 A | 7/1977 | Foucras | 219/301 |
| 4,111,209 A | 9/1978 | Wolvek et al. | 128/400 |
| 4,246,932 A | 1/1981 | Raines | 137/512 |

(Continued)

FOREIGN PATENT DOCUMENTS

WO    WO 91/05528    2/1991

OTHER PUBLICATIONS

Long, R., "Regional Cranial Hypothermia in the Prevention of Cerebral Ischemic Damage During Carotid Occlusion", *Review of Surgery*, vol. 23, No. 3, May 1966, pp. 226-228.

(Continued)

*Primary Examiner*—Roy D. Gibson
(74) *Attorney, Agent, or Firm*—Robert D. Buyan; Stout, Uxa, Buyan & Mullins, LLP

(57) ABSTRACT

The present invention provides a method and apparatus for controlling the internal body temperature of a patient. According to the present invention, a catheter is inserted through an incision into a large blood vessel of a patient. By selectively heating or cooling a portion of the catheter lying within the blood vessel, heat may be transferred to or from blood flowing within the vessel and the patient's body temperature may thereby be increased or decreased as desired. The invention will find use in treating undesirable conditions of hypothermia and hyperthermia, or for inducing a condition of artificial hypothermia when desired.

31 Claims, 9 Drawing Sheets

U.S. PATENT DOCUMENTS

| | | | |
|---|---|---|---|
| 4,298,006 A | 11/1981 | Parks | 607/106 |
| 4,378,797 A | 4/1983 | Osterholm | 604/24 |
| 4,445,500 A | 5/1984 | Osterholm | 128/1 |
| 4,445,886 A | 5/1984 | Osterholm | 604/28 |
| 4,470,407 A | 9/1984 | Hussein | 128/6 |
| 4,540,402 A | 9/1985 | Aigner | 604/24 |
| 4,661,094 A | 4/1987 | Simpson | 604/53 |
| 4,662,383 A | 5/1987 | Sogawa et al. | 128/784 |
| 4,672,962 A | 6/1987 | Hershenson | 128/303 |
| 4,686,085 A | 8/1987 | Osterholm | 422/45 |
| 4,701,166 A | 10/1987 | Groshong et al. | 604/247 |
| 4,705,501 A | 11/1987 | Wigners et al. | 604/43 |
| 4,748,979 A | 6/1988 | Hershenson | 128/303.1 |
| 4,750,493 A | 6/1988 | Brader | 128/380 |
| 4,754,752 A | 7/1988 | Ginsburg et al. | 128/303 |
| 4,769,005 A | 9/1988 | Ginsburg et al. | 604/53 |
| 4,804,358 A | 2/1989 | Karcher et al. | 600/17 |
| 4,819,655 A | 4/1989 | Webler | 128/713 |
| 4,840,617 A | 6/1989 | Osterholm | 604/174 |
| 4,857,054 A | 8/1989 | Helfer | 604/102 |
| 4,892,095 A | 1/1990 | Nakhgevany | 128/207.14 |
| 4,892,519 A | 1/1990 | Songer et al. | 604/96 |
| 4,899,741 A | 2/1990 | Bentley et al. | 606/27 |
| 4,909,252 A | 3/1990 | Goldberger | 606/194 |
| 4,920,963 A | 5/1990 | Brader | 128/402 |
| 4,941,475 A * | 7/1990 | Williams et al. | 600/505 |
| 4,976,691 A | 12/1990 | Sahota | 604/96 |
| 4,995,863 A | 2/1991 | Nichols et al. | 604/247 |
| 5,019,075 A | 5/1991 | Spears et al. | 607/113 |
| 5,030,210 A | 7/1991 | Alchas | 604/247 |
| 5,041,089 A | 8/1991 | Mueller et al. | 606/28 |
| 5,092,841 A | 3/1992 | Spears | 604/96 |
| 5,106,360 A | 4/1992 | Ishiwara et al. | 600/2 |
| 5,112,301 A | 5/1992 | Fenton, Jr. et al. | 604/30 |
| 5,147,355 A * | 9/1992 | Friedman et al. | 606/23 |
| 5,147,385 A | 9/1992 | Beck et al. | 623/1 |
| 5,149,321 A | 9/1992 | Klatz et al. | 604/52 |
| 5,151,100 A | 9/1992 | Abele et al. | 606/28 |
| 5,180,364 A | 1/1993 | Ginsburg | 604/280 |
| 5,269,758 A * | 12/1993 | Taheri | 604/96.01 |
| 5,342,301 A * | 8/1994 | Saab | 604/103.13 |
| 5,383,856 A | 1/1995 | Bersin | 604/103 |

OTHER PUBLICATIONS

White, R. et al., "Profound selective cooling and ischemia of primate brain without pump or oxygenator", Surgery, vol. 66, No. 1, Jul. 1969, pp. 224-232.

Weale, F.E., "The Aneroid Manometer in Peripheral Arterial Surgery", The British Journal of Surgery, vol. 56, No. 8, Aug. 1969, pp. 612-631.

Negrin, Jr., J., "The Hypothermostat: An Instrument to Obtain Local Hypothermia of the Brain or Spinal Cord", International Surgery, Sec. 1, vol. 54, No. 2, Aug. 1970, pp. 93-106.

Safar, P., "Resuscitation after global brain ischemia-anoxia", Crit. Care Med., vol. 6, No. 4, (1978), pp. 215-227.

Ping, F. et al., "Protection of the Brain from Hypoxia: A Review", Canad. Anaesth. Soc. J., vol. 25, No. 6, Nov. 1978, pp. 468-473.

Safar, P., "Dynamics of Brain Resuscitation After Ischemic Anoxia", Hospital Practice, Feb. 1981, pp. 67-72.

Gisvold, S. et al., "Multifaceted Therapy After Global Brain Ischemia in Monkeys", Stroke, vol. 15, No. 5, Sep. 1984, pp. 803-812.

Leonov, Y. et al., "Mild Cerebral Hypothermia during and after Cardiac Arrest Improves Neurologic Outcome in Dogs", Journal of Cerebral Blood Flow and Metabolism, vol. 10, (1990), pp. 57-70.

Minamisawa, H. et al., "The Effect of Mild Hyperthermia and Hypothermiaon Brain Damage Following 5, 10 and 15 Minutes of Forebrain Ischemia", American Neurological Association, (1990), pp. 26-33.

Tisherman, S. et al. "Therapeutic Deep Hypothermic Circulatory Arrest in Dogs: A Resuscitation Modality for Hemorrahagic Shock with 'Irreparable' Injury", The Journal of Trauma, vol. 30, No. 7, Jul. 1990, pp. 836-847.

Tisherman, S. et al., "Deep Hypothermic Circulatory Arrest Induced During Hemorrhagic Shock in Dogs: Preliminary Systemic and Cerebral Metabolism Studies", Current Surgery, Sep. 1990, pp. 327-330.

Leonov, Y. et al., "Moderate Hypothermia After Cardiac Arrest of 17 Minutes in Dogs: Effect on Cerebral and Cardiac Outcome", Stroke, vol. 21, No. 11, Nov. 1990, pp. 1600-1606.

Sterz, F. et al., "Mild Hypothermic Cardiopulmonary Resuscitation Improves Outcome after Prolonged Cardiac Arrest in Dogs", Critical Care Medicine, vol. 19, No. 3, (1991), pp. 379-389.

Tisherman, S. et al., "Profound Hypothermia (<10° C) Compared with Deep Hypothermia (15° C) Improves Neurologic Outcome in Dogs After Two Hours' Circulatory Arrest Induced to Enable Resuscitative Surgery", The Journal of Trauma, vol. 31, No. 8, Aug. 1991, pp. 1051-1062.

Dietrich, W., "The Importance of Brain Temperature in Cerebral Injury", Journal of Neurotrauma, vol. 9, Suppl. 2, (1992), pp. S475-S485.

Ginsberg, M. et al., "Therapeutic Modulation of Brain Temperature: Relevance to Ischemic Brain Injury", Cerebrovascular and Brain Metabolism Reviews, vol. 4, No. 3, (1992), pp. 189-225.

Martinez-Arizala, A. et al., "Hypothermia in Spinal Cord Injury", Journal of Neurotrauma, vol. 9, Suppl. 2, (1992), pp. S497-S505.

Weinrauch, V. et al., "Beneficial Effect of mild Hypothermia and Detrimental Effect of Deep Hypothermia After Cardiac Arrest in Dogs", Stroke, vol. 23, No. 10, Oct. 1992, pp. 1454-1462.

Kuboyama, K. et al., "Delay in cooling negates the beneficial effect of mild resuscitative cerebral hypothermia after cardiac arrest in dogs: A prospective, randomized study", Crit. Care Med., vol. 21, No. 9, (1993), pp. 1348-1358.

Maher, J. et al., "Hypothermia as a Potential Treatment for Cerebral Ischemia", Cerebrovascular and Brain Metabolism Reviews, vol. 5, No. 4, (1993), pp. 277-300.

Safar, P., "Cerebral Resuscitation After Cardiac Arrest: Research Initiatives and Future Directions", Annals of Emergency Medicine, vol. 22, No. 2, Part 2, Feb. 1993, pp. 324-389.

A Technique for The Production of Hypothermia: Prelim. Report Charles B. Ripstein, MD, et al.; Dept of Surgery, Maimonides Hospital and State Univ. of NY, College of Medicine at N.Y.; Apr. 7, 1953.

Effects of Total Body Core Cooling of Heat Production of Conscious Goats; James B. Mercer & Claus Jessen; Pflugers Archiv European Journal of Physiology; Springer-Verlag 1978.

Jessen, C. et al., "Intravascular Heat Exchanger for Conscious Goats", Pflugers Archiv European Journal of Physiology, vol. 368, (1977) pp. 263-265.

* cited by examiner

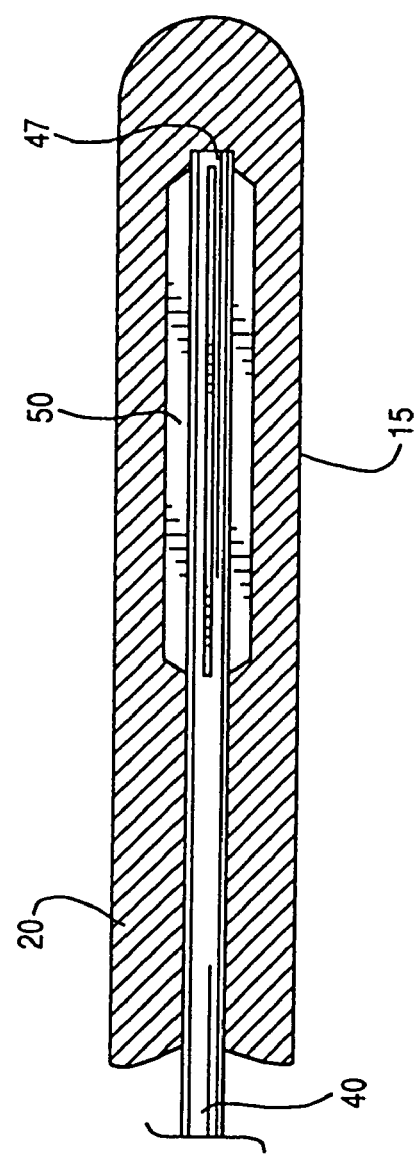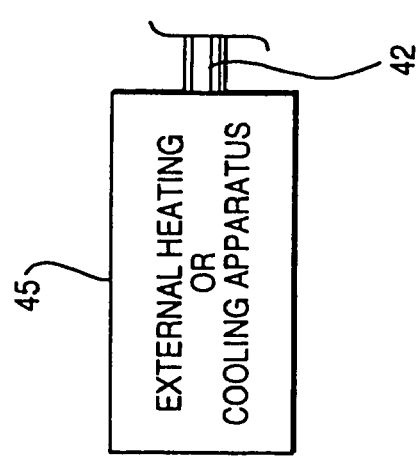
FIG. 5

METHOD FOR CONTROLLING A PATIENT'S BODY TEMPERATURE

RELATED APPLICATIONS

This is a continuation of co-pending U.S. patent application Ser. No. 09/943,552 filed Aug. 30, 2001, now U.S. Pat. No. 6,656,209 which is a continuation of Ser. No. 09/130,852 filed Aug. 7, 1998 and now issued as U.S. Pat. No. 6,306,161, which is a division of Ser. No. 09/100,275 filed Jun. 19, 1998 now issued as U.S. Pat. No. 6,110,168, which is a continuation-in-part of Ser. No. 08/584,013, filed Jan. 8, 1996 and now issued as U.S. Pat. No. 5,837,003, which is a continuation-in-part of Ser. No. 08/324,853 filed Oct. 18, 1994 now issued as U.S. Pat. No. 5,486,208, which is a continuation of Ser. No. 08/015,774 filed Feb. 10, 1993. The specification of this application is identical to the specification of Ser. No. 08/015,774 filed Feb. 10, 1993 and all claims are subject to the Feb. 10, 1993 filing date.

BACKGROUND OF THE INVENTION

1. Field of the Invention

The present invention relates generally to the selective modification and control of a patient's body temperature. More particularly, the present invention provides methods and apparatus for treating hypothermia or hyperthermia by inserting a catheter into a blood vessel of the patient and selectively controlling the temperature of a portion of the catheter within the blood vessel. Heat is transferred to or from blood flowing through the vessel and the patient's body temperature may thereby be increased or decreased as desired.

2. Description of the Background Art

Under ordinary circumstances the thermoregulatory system of the human body maintains a near constant temperature of about 37° C. (98.6° F.). Heat lost to the environment is precisely balanced by heat produced within the body.

Hypothermia is a condition of abnormally low body temperature. Hypothermia can be clinically defined as a core body temperature of 35° C. or less. Hypothermia is sometimes characterized further according to its severity. A body core temperature in the range from 32° C. to 35° C. is described as "mild" hypothermia, 30° C. to 32° C. is called "moderate," 24° C. to 30° C. is described as "severe," and a body temperature less than 24° C. constitutes "profound" hypothermia. Although the above ranges provide a useful basis for discussion, they are not absolutes and definitions vary widely in the medical literature.

Accidental hypothermia results when heat loss to the environment exceeds the body's ability to produce heat internally. In many cases, thermoregulation and heat production are normal but the patient becomes hypothermic due to overwhelming environmental cold stress. This is a relatively common condition, often resulting from exposure to the elements. Hypothermia may also occur in patients exposed to mild cold stress whose thermoregulatory ability has been lessened due to injury or illness. For example, this type of hypothermia sometimes occurs in patients suffering from trauma or as a complication in patients undergoing surgery.

Hypothermia of either type is a dangerous condition which can have serious medical consequences. In particular, hypothermia interferes with the ability of the heart to pump blood. Hypothermia may be fatal for this reason alone. Additionally, low body temperature seriously interferes with the enzymatic reactions necessary for blood clotting. This sometimes results in bleeding that is very difficult to control, even when normal clotting factor levels are present. These effects and other adverse consequences of hypothermia lead to drastically increased mortality rates both among victims of trauma and in patients undergoing surgery.

Simple methods for treating hypothermia have been known since very early times. Such methods include wrapping the patient in blankets, administering warm fluids by mouth, and immersing the patient in a warm water bath. Even these simple methods may be effective if the hypothermia is not too severe. These simple methods are limited in their effectiveness however. Wrapping the patient in blankets ultimately depends on the patient's own production of heat to rewarm his body. In even moderate cases of hypothermia, or in the case of an ill or injured patient, the patient may simply be too weak or exhausted to produce sufficient heat. Oral administration of a warm fluid requires that the patient be conscious and capable of swallowing the fluid. Since loss of consciousness occurs early in hypothermia, this method is also limited to moderate cases. Finally, immersion of the patient in a warm water bath is often simply impractical. For example, immersion of a patient undergoing surgery would obviously be undesirable. Furthermore, the immersion technique is time consuming and may be ineffective in that it requires the transmission of warmth from the patient's skin surface into the body core before the benefit of the warmth can be realized.

For this reason, methods have been devised to allow for the direct warming of a patient's blood. These methods involve removing blood from the patient, warming the blood in external warming equipment, and delivering the blood back into the patient. While such methods are much more effective than any of the simple methods previously described, they are disadvantageous for other reasons. First, the apparatus involved is quite cumbersome. Second, some danger is involved in even the temporary removal of significant quantities of blood from an already weakened patient. In fact, a further drop in body temperature is often experienced when blood is first removed for warming in the external apparatus. It would be desirable for these reasons to provide a method and apparatus for directly warming blood in situ, i.e., within the patient's body.

Hyperthermia, a condition of abnormally high body temperature, may result from exposure to a hot environment, overexertion, or fever. Body core temperatures can range from 38° C.-41° C. due to fever and may be substantially higher in cases of exposure and overexertion. Like hypothermia, hyperthermia is a serious condition and can be fatal. Also like hypothermia, simple methods for treating hyperthermia, for example, immersion of the patient in a cool water bath or administration of cool fluids, have long been known. Generally, these simple methods for treating hyperthermia suffer from the same drawbacks and limited effectiveness as the simple hypothermia treatments noted above.

It would therefore be desirable to develop more effective methods for lowering the body temperature of hyperthermic patients. Furthermore, it is sometimes beneficial to induce an artificial low-temperature condition (induced hypothermia) within a patient by artificial cooling. This may be desirable, for example, to reduce a patient's requirement for oxygen during surgery or during a condition of cardiovascular collapse.

To achieve these goals, methods have been used in which a patient's blood is removed from his body, cooled in external cooling apparatus, and returned to his body. This external cooling suffers from the same disadvantages as the external warming previously described. External cooling requires cumbersome apparatus and the temporary removal of blood entails some degree of risk to the patient. It would therefore be desirable to devise a method and apparatus for cooling blood within the patient's body.

SUMMARY OF THE INVENTION

The present invention provides methods and apparatus for modifying and controlling a patient's body temperature. According to the present invention, a catheter is inserted percutaneously into a blood vessel of the patient. By controlling the temperature of a portion of the catheter lying within the blood vessel, heat may be selectively transferred to or from blood flowing through the vessel. The patient's body temperature may thereby be increased or decreased as desired. Some embodiments of apparatus suitable for practicing the present invention will provide means for treating hypothermia by warming a patient's blood. Other embodiments will provide means for treating hyperthermia or inducing a desired condition of hypothermia by cooling the patient's blood.

Because blood circulates rapidly through the vascular system, the beneficial effect of warming or cooling blood within the vessel will be quickly felt throughout the patient's body. In situ modification of blood temperature is further advantageous in that blood is not removed from the patient. Additionally, no external pump is needed to circulate the blood. Injury to blood components from the pump is thereby eliminated. Furthermore, the required apparatus is much simpler, less cumbersome, and easier to use than the external blood warming or cooling apparatus previously known.

A catheter suitable for practicing the present invention will include means for warming or cooling at least a portion of the catheter inserted into the blood vessel. It is desirable that such a catheter have a relatively small cross-section so as not to unnecessarily impede blood flow through the vessel. On the other hand, a large heat transfer surface area will facilitate rapid heat transfer between the catheter and the blood. Structural features may therefore be included to increase the surface area of the temperature controlled region.

BRIEF DESCRIPTION OP THE DRAWINGS

FIG. 5 depicts a catheter in which heat is transferred down a thermally conductive shaft between the distal end of the catheter and heating or cooling apparatus at the proximal end of the shaft;

DESCRIPTION OP SPECIFIC EMBODIMENTS

The present invention provides methods and apparatus for selectively modifying and controlling a patient's body temperature by warming or cooling the patient's blood in situ. According to the present invention, a catheter is inserted through a puncture or incision into a blood vessel in the patient's body. By warming or cooling a portion of the catheter, heat may be transferred to or from blood flowing within the vessel and the patient's body temperature may thereby be increased or decreased as desired. During the procedure, the patient's body core temperature may be independently monitored and treatment may continue until the patient's core temperature approaches the desired level, usually the normal body temperature of about 37° C. Such methods will find use in treating undesirable conditions of hypothermia and hyperthermia and may also be used to induce an artificial condition of hypothermia when desired, e.g., to temporarily reduce a patient's need for oxygen. In such a case, the patient's temperature may be reduced several degrees Celsius below the normal body temperature.

Figure 1:
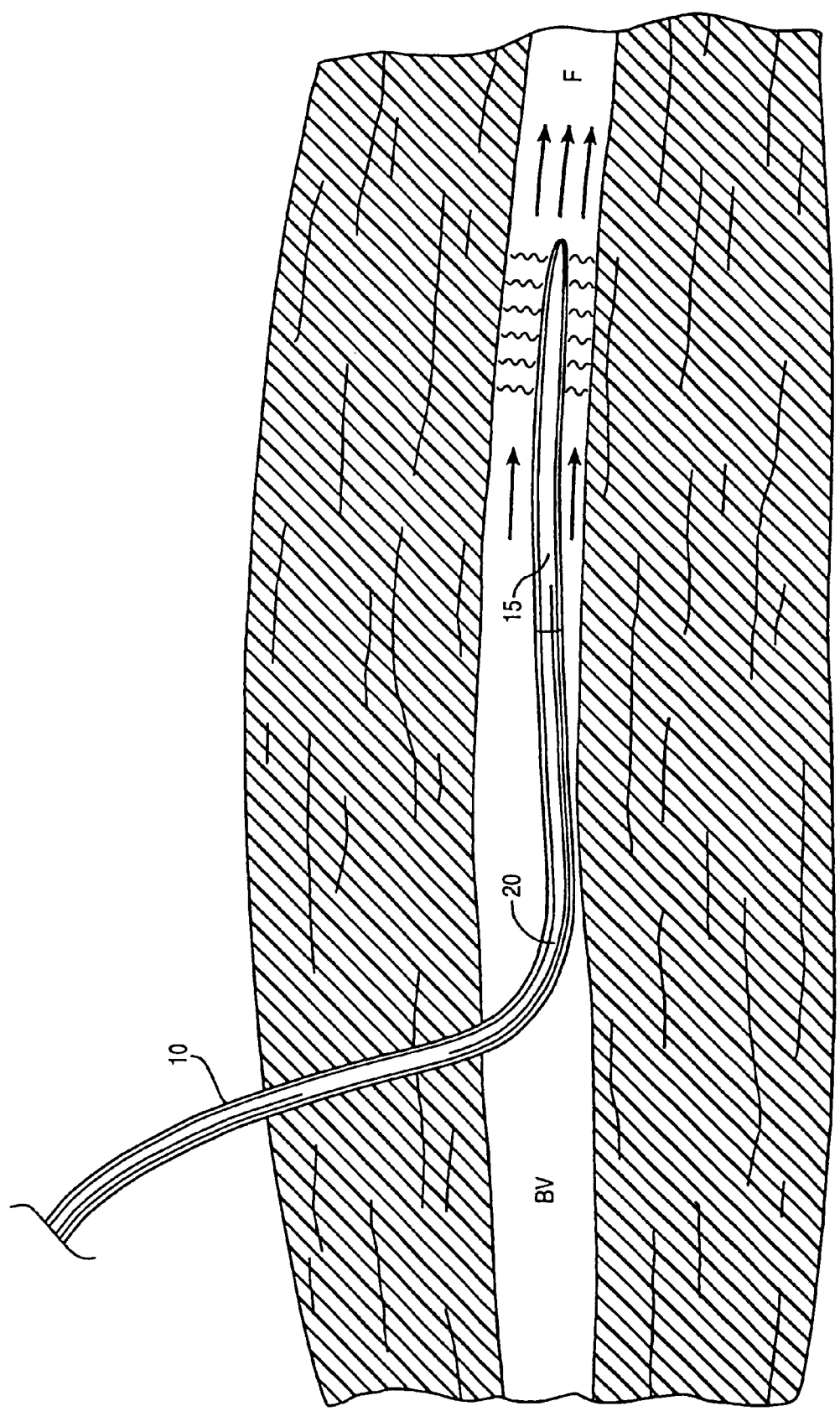
FIG. 1 depicts a catheter according to the present invention inserted percutaneously into a blood vessel of a patient.

FIG. 1 depicts a distal end 15 of a catheter 10 according to the present invention. The catheter has been inserted through the patient's skin into a blood vessel BV. Blood flow through the vessel is indicated by a set of flow arrows F. Preferably, the catheter will be inserted into a relatively large blood vessel, e.g., the femoral artery or vein or the jugular vein. Use of these vessels is advantageous in that they are readily accessible, provide safe and convenient insertion sites, and have relatively large volumes of blood flowing through them. In general, large blood flow rates facilitate quicker heat transfer into or out of the patient.

For example, the jugular vein may have a diameter of about 22 French, or a bit more than 7 millimeters (1 French 0.013 inches=0.33 mm). A catheter suitable for insertion into a vessel of this size can be made quite large relative to catheters intended for insertion into other regions of the vascular system. Atherectomy or balloon angioplasty catheters are sometimes used to clear blockages from the coronary artery and similar vessels. These catheters commonly have external diameters in the range between 2 and 8 French.

In contrast, it is anticipated that a catheter according to the present invention will typically have an external diameter of about 10 French or more, although this dimension may obviously be varied a great deal without departing from the basic principles of the claimed invention. It is desirable that the catheter be small enough so that the puncture site can be entered using the percutaneous Seldinger technique, a technique well known to medical practitioners. To avoid vessel trauma, the catheter will usually be less than 12 French in diameter upon insertion. Once in the vessel however, the distal or working end of the catheter can be expanded to any size so long as blood flow is not unduly impeded.

Additionally, the femoral artery and vein and the jugular vein are all relatively long and straight blood vessels. This will allow for the convenient insertion of a catheter having a temperature controlled region of considerable length. This is of course advantageous in that more heat may be transferred at a given temperature for a catheter of a given diameter if the length of the heat transfer region is increased.

Techniques for inserting catheters into the above mentioned blood vessels are well known among medical personnel. Although the method of the present invention will probably be most commonly employed in a hospital, the procedure need not be performed in an operating room. The apparatus and procedure are so simple that the catheter may be inserted and treatment may begin in some cases even in an ambulance or in the field.

The distal end 15 of the catheter may be heated or cooled as desired and held at a temperature either somewhat above or somewhat below the patient's body temperature. Blood flowing through the vessel will thereby be warmed or cooled. That blood will be circulated rapidly throughout the patient's circulatory system. The beneficial effect of warming or cooling the patient's blood in the vicinity of the catheter will thereby be spread very quickly throughout the entire body of the patient.

Figure 2:
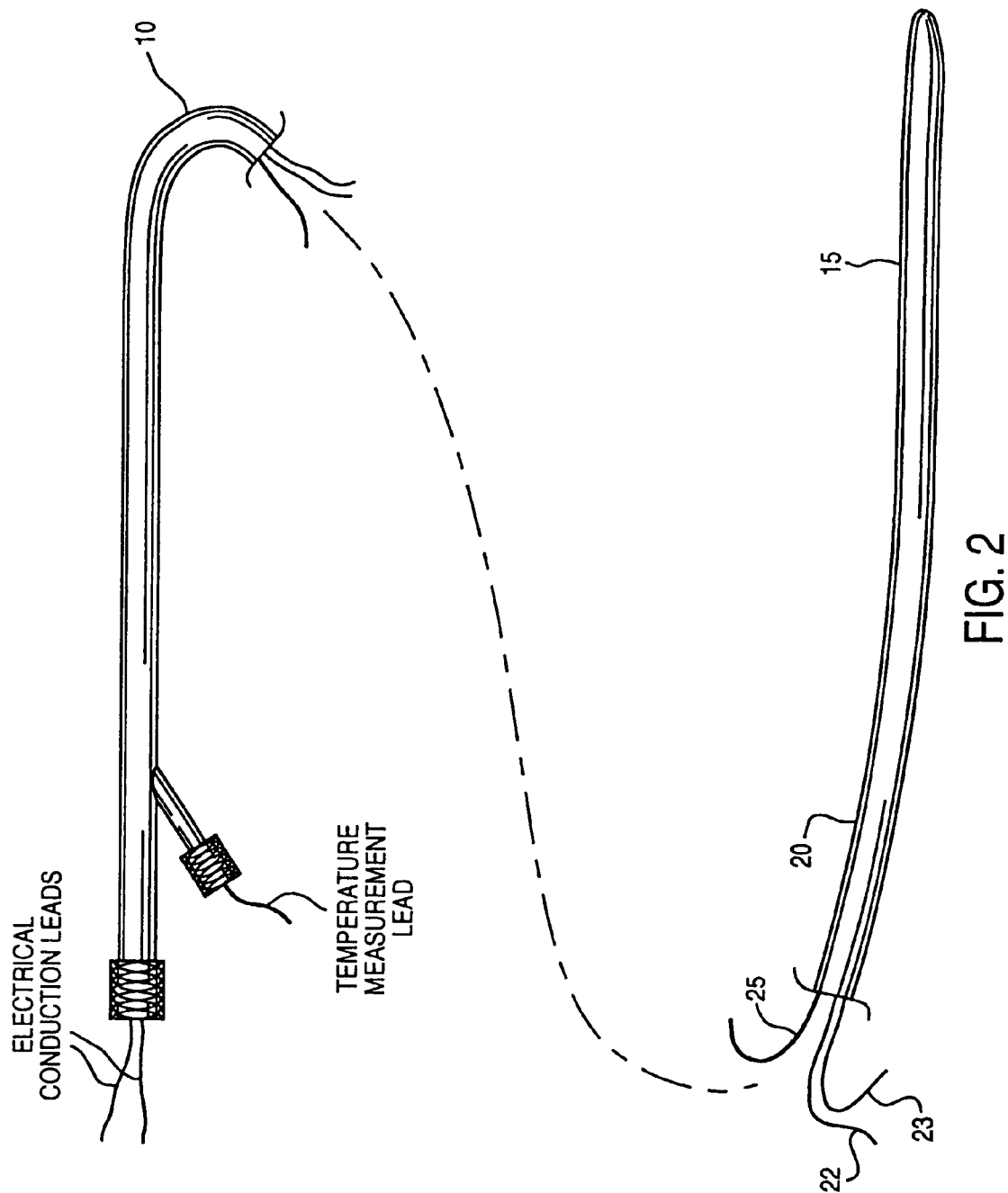
FIG. 2 depicts a catheter suitable for increasing the temperature of a patient's blood by electrical resistance heating.
Figure 3:
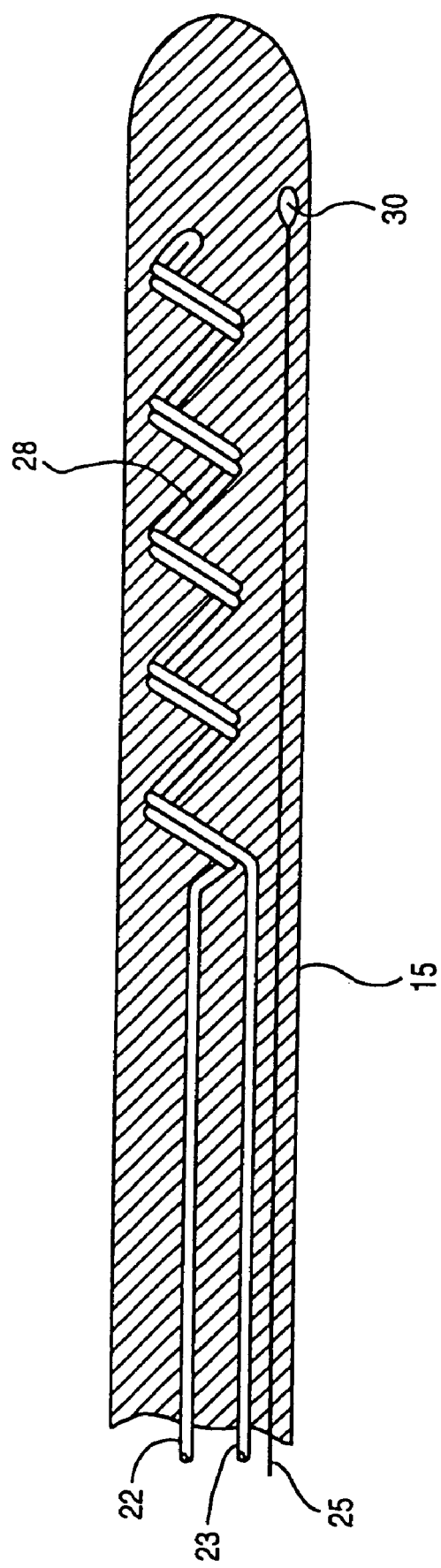
FIG. 3 depicts the distal end of a catheter having a resistance heating element and a temperature sensor.

FIGS. 2 and 3 depict a catheter suitable for treating hypothermia by increasing the temperature of a patient's blood. As depicted in FIG. 2, the catheter has a preferably flexible catheter body 20. Disposed within the catheter body are a pair of electrical conduction leads 22 and 23 and a temperature measurement lead 25.

Electrical conduction leads 22 and 23 are connected to a resistance heating element 28, as depicted in FIG. 3. Electrical current provided by a power source (not shown) is converted to heat within the heating coil. That heat warms distal end 15 of the catheter and is thereby transferred to blood flowing through the vessel.

Temperature measurement lead 25 is connected to a temperature sensor 30. The temperature sensor facilitates the control of current flow through the heating coil. It is important to closely monitor the temperature of the distal end of the catheter and thus the flow of heat into the patient's blood. Care must be taken not to overheat the blood while still providing an adequate rate of heat transfer into the patient. The provision of a sensitive temperature sensor at the distal end of the catheter will help to achieve this goal.

Figure 4:
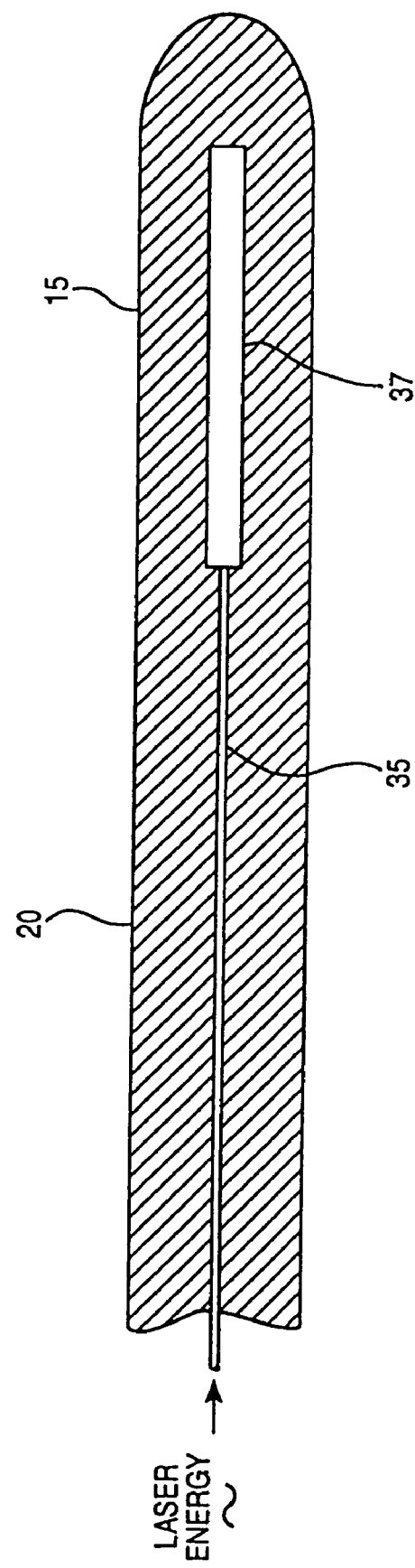
FIG. 4 depicts the distal end of a catheter having an optical wave guide and an optical diffusing tip for converting laser energy into heat.

FIG. 4 depicts an alternate embodiment of a catheter having means for transferring energy from an external power source to distal end 15 of catheter body 20. In this embodiment, laser energy from a laser light source (not shown) is transmitted along optical wave guide 35. The wave guide directs the laser energy into optical diffusing tip 37, which converts the laser energy to heat. From diffusing tip 37, the heat radiates outward into distal end 15 of the catheter and from there into the patient's blood stream.

FIG. 5 depicts another catheter suitable for practicing the present invention. This embodiment has a thermally conductive shaft 40 running the length of catheter body 20. Shaft 40 is made of a metal or other material having a high thermal conductivity. By heating or cooling the proximal end 42 of shaft 40 with an external heating or cooling apparatus 45, heat will be caused to flow either into or out of the distal end 47 of the shaft. In the embodiment depicted, the distal end of the shaft is fitted with heat transfer vanes 50, which add to the surface area of the shaft and thereby promote more effective heat transfer between the catheter and the patient's blood stream.

Figure 6:
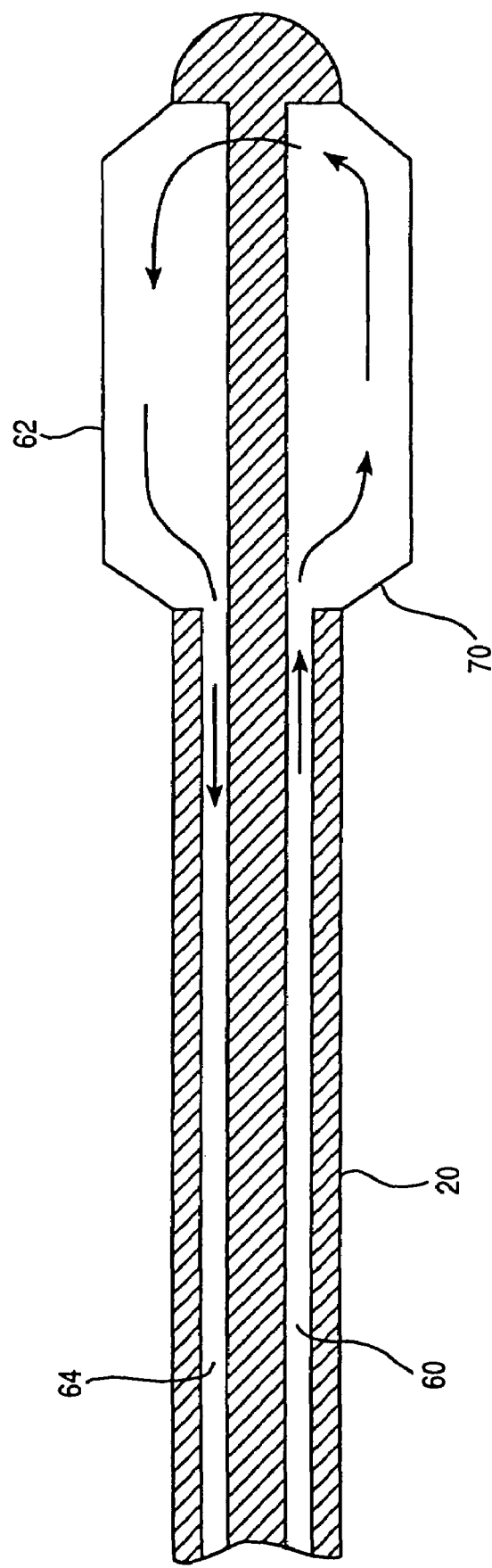
FIG. 6 depicts a catheter in which a heated or cooled fluid flows through a balloon, which provides for an increased surface area at the distal end.

FIG. 6 depicts still another means for transferring heat to or from the distal end of a catheter. In this embodiment, catheter body 20 has two lumens running through it. Fluid flows from the proximal end of the catheter through in-flow lumen 60, through a heat transfer region 62, and back out through out-flow lumen 64. By supplying either warmed or cooled fluid through inflow lumen 60, heat may be transferred either to or from the patient's blood stream.

In the embodiment depicted, heat transfer region 62 is in the form of a balloon 70. Use of a balloon will be advantageous in some embodiments to provide an increased surface area through which heat transfer may take place. Balloon inflation is maintained by a pressure difference in the fluid as it flows through in-flow lumen 60 and out-flow lumen 64. The balloon should be inflated to a diameter somewhat less than that of the inside diameter of the blood vessel so as not to unduly impede the flow of blood through the vessel.

Figure 7:
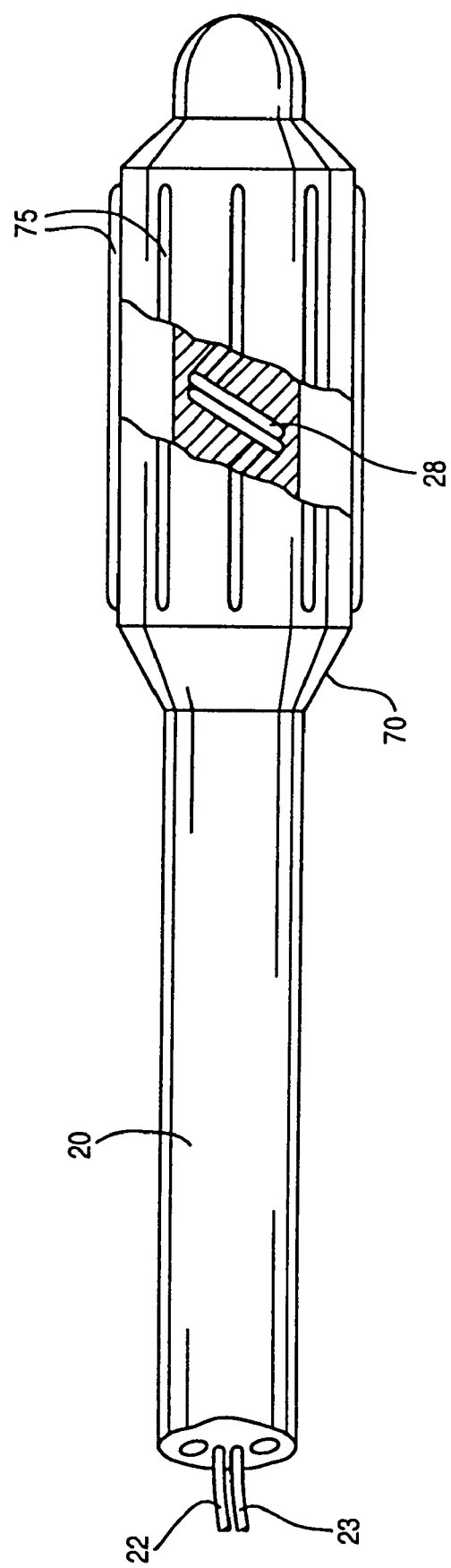
FIG. 7 depicts a catheter having a resistance heating element at its distal end and a balloon having longitudinal ribs to further increase the heat transfer surface area.
Figure 8A:
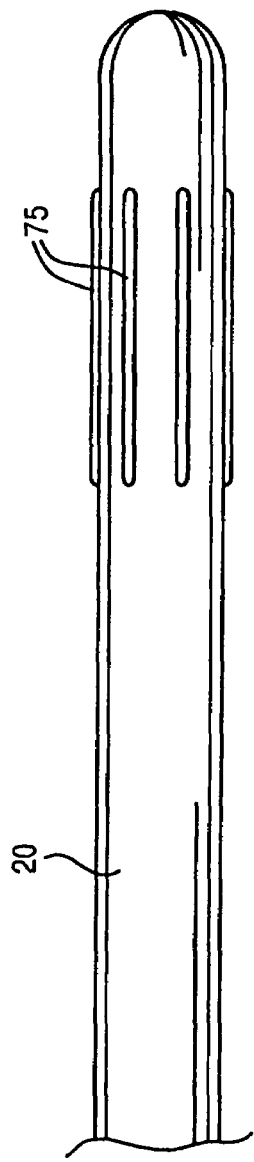
FIG. 8A depicts a catheter having longitudinal fins at the distal end of the catheter body.
Figure 8B:
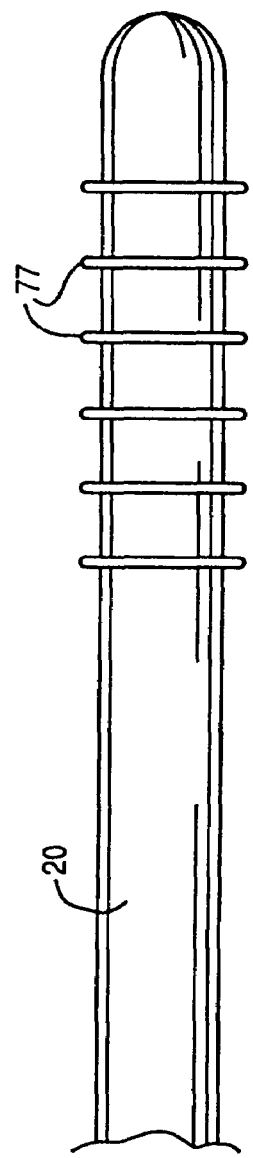
FIG. 8B depicts a catheter having radial ribs at the distal end of the catheter body.
Figure 8C:
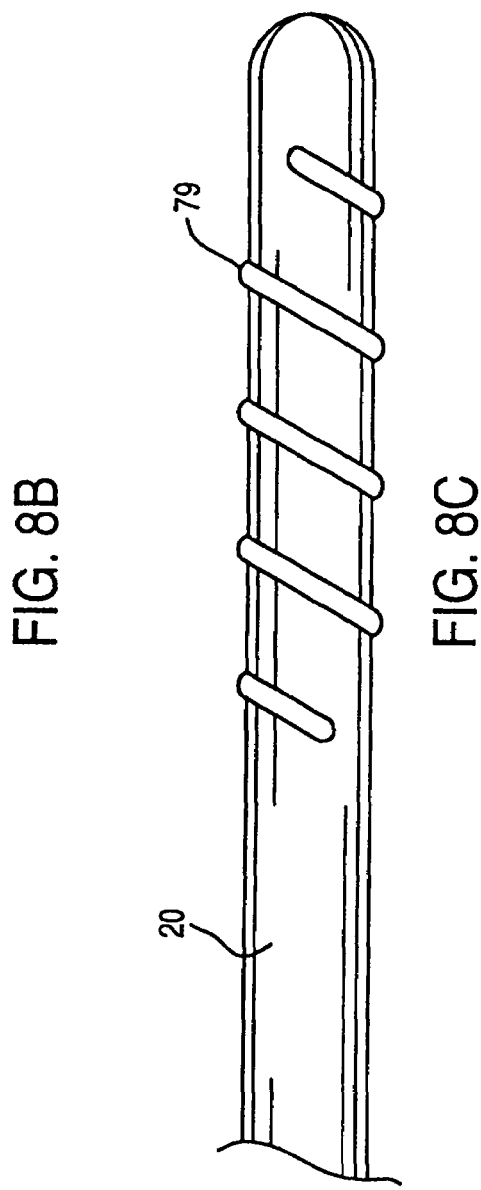
FIG. 8C depicts a catheter having a spiral fin to increase the heat transfer area at the distal end of the catheter.

FIG. 7 depicts a catheter having an internal resistance heating element 28 and a balloon 70, which is shown inflated. In this embodiment, the increased surface area provided by the inflated balloon is further augmented by the presence of a set of longitudinal fins 75 on the surface of the balloon. Alternatively, longitudinal fins 75, radial ribs 77, or one or more spiral fins 79 may be disposed directly on the body 20 of a catheter as shown in FIGS. 8A, 8B and 8C. Ordinarily, longitudinal ribs will be most advantageous because they restrict blood flow through the vessel less than other configurations. In fact, these ribs insure that the balloon will not block the flow of blood through the vessel because a flow path will always be maintained (between the ribs) regardless of how much the balloon is inflated.

Inclusion of a balloon on a catheter employing resistance heating allows for designs in which current is conducted through the fluid which fills the balloon. The catheter depicted in FIG. 9 has a catheter body 20 about which is disposed an inflatable balloon 70. The balloon is inflated by injecting a suitable fluid into the balloon through central balloon inflation lumen 80. In this embodiment, current flows from an external source of electrical power (not shown) through conduction wires 82 and 84 to electrodes 86 and 88.

A suitable fluid will allow current to flow between electrodes 86 and 88. Common saline solution, for example, contains dissolved ions which can serve as charge conductors. Electrical resistance within the fluid will cause the fluid to be heated, thus providing the desired warming of the catheter. The amount of warming will be dependant upon the voltage between the electrodes, the distance between them, and the resistivity of the fluid. The relation between these quantities is fairly simple; one skilled in the art will have no difficulty selecting appropriate values.

Figure 9:
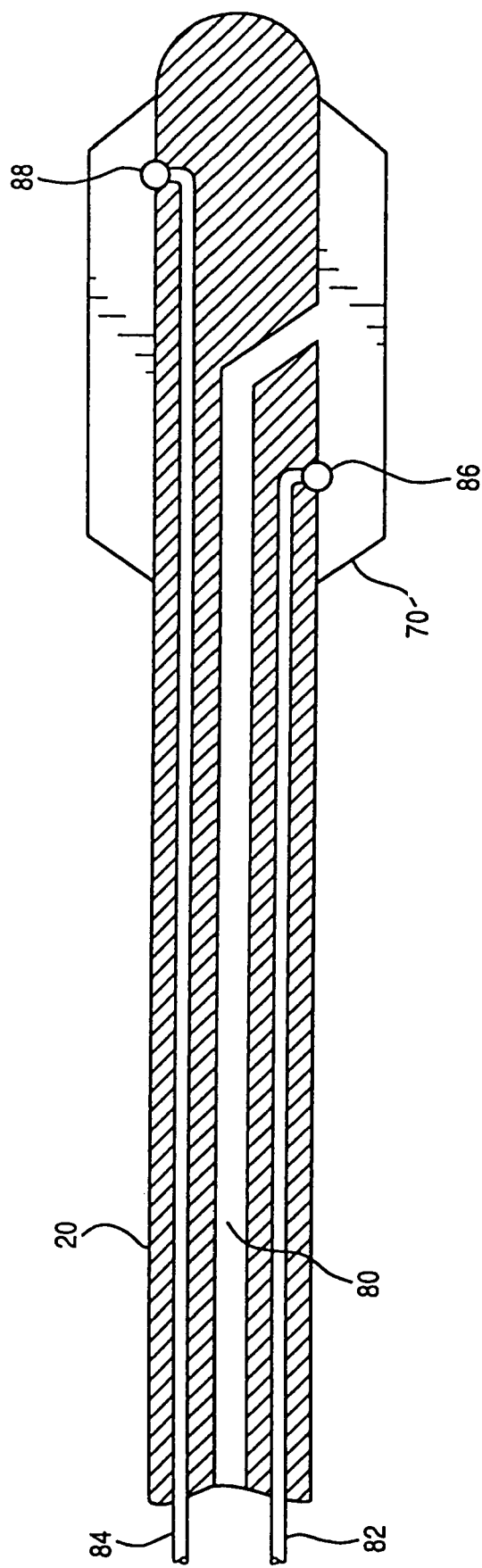
FIG. 9 depicts a catheter having a distal end covered by an inflatable balloon filled with a suitable fluid through which a current is conducted.

Resistance heating catheters like those depicted in FIGS. 3, 7 and 9 may use DC or low frequency AC power supplies. However, it may be desirable to use a higher frequency power supply. For example, it is known that the risk of adverse physiological response or electrocution response may be lessened at frequencies within the range of about 100 kilohertz to 1 megahertz. Power supplies that operate at these frequencies are commonly referred to as radio-frequency, or RF, power supplies.

A catheter according to the present invention should be designed to optimize the rate of heat transfer between the catheter and blood flowing through the vessel. While a large surface area is desirable in order to maximize heat transfer, care must be taken so that the catheter does not unduly restrict blood flow through the vessel. Furthermore, the temperature of the catheter should be carefully controlled to prevent undesirable chemical changes within the blood. This is especially important when applying heat to the blood as blood is readily denatured by even moderately high temperatures. The exterior temperature of a catheter for warming blood should generally not exceed about 42° C.-43° C.

It is estimated that a catheter whose surface temperature is controlled between 37° C. and 42° C. will provide a body core warming rate of approximately one to two degrees Celsius per hour in a patient starting out with severe hypothermia. This estimate is highly dependant on a number of factors including the rate of blood flow through the vessel, the initial body temperature of the patient, the external surface area of the catheter through which heat is conducted, etc. The actual rate achieved may vary substantially from the above estimate.

The above estimate provides a starting point for a rough estimate as to the level of power transferred from the catheter to the patient's body and therefore of the size of the power supply required by the system. Regardless of the exact means of power transmission chosen, resistance heating coil, laser and diffusing tip, direct conduction or fluid circulation, an appropriate power supply will be required to provide heat to the system.

The sum of heat entering and leaving a patient's body can be written as:

$$\Delta H = H_c + H_i - H_e$$

where $\Delta H$ is the sum of all heat transferred, $H_c$ is the heat transferred from the catheter to the patient, $H_i$ the heat produced by the patient internally, and $H_e$ the heat lost from the patient to the environment. If one assumes, as will ordinarily be the case in a healthy patient, that the body's internal thermoregulatory system will produce just enough heat to offset heat lost to the environment, then the equation is made simple:

$$\Delta H = H_c.$$

The above equation can be written in terms of the change in the patient's internal body temperature over time as follows:

$$mc(\Delta T/\Delta t) = (\Delta H_c/\Delta t)$$

where m is the body mass of the patient, c is the specific heat of the patient's body, $(\Delta T/\Delta t)$ is the time rate of change of the patient's internal body temperature, $(\Delta H_c/\Delta t)$ is the time rate of heat delivery from the catheter to the patient.

If one assumes a patient having a body mass of 75 kilograms and a specific heat of 4186 joules/° C.-kg (assumes the specific heat of the human body to be the same as that of water, the actual value will be somewhat different), then a warming rate of 1° C. per hour (3600 seconds) will require the catheter to transfer heat to the patient at a rate of about 87 watts (1 watt=1 joule/sec).

However, as an estimate of the desirable size of a power supply to be used with a catheter of the present invention, this estimate is almost certainly too low. This is true for a number of reasons. First, it was assumed for the sake of convenience that the patient's internal system would produce an amount of heat equal to that lost to the environment. In a hypothermic patient this will obviously not be the case. Almost by definition, hypothermia occurs when a person's ability to produce heat internally is overwhelmed by heat lost to the environment. The catheter will have to make up the difference so the power level required will need to be greater for that reason alone.

Additionally, the above estimate does not allow for power losses between the power supply and whatever warming means is utilized. Such losses could include resistance losses in electrical transmission lines between the power supply and a resistance heating element, inherent inefficiencies and other losses in a system having a laser and a diffusing tip, heat losses along a thermally conductive shaft or fluid circulation lumen, and the like. Any such losses which do occur will need to be compensated for by additional power supply capacity.

Furthermore, it would be undesirable to limit the performance of a catheter according to the present invention by limiting the size of the power supply used. It would be preferable instead to use a power supply capable of providing power considerably in excess of that actually needed and then controlling the delivery of that power according to the measured temperature of the catheter itself. As mentioned previously, this can be readily accomplished by including a sensitive temperature sensor within the body of the catheter. Nevertheless, the above calculation can be used as a useful estimate of the likely lower bound for sizing a power supply for use in a catheter according to the present invention.

An alternative estimate can be made by comparing the likely performance of the various embodiments described herein with the power requirements for the external blood warming apparatus presently known. Such external warming apparatus generally requires a supply of power on the order of 1000-1500 watts and sometimes more. A device according to the present invention will most likely require considerably less power than that. First, the present invention requires no external pump to circulate the blood; this function is provided by the patient's own heart. Accordingly, no power is needed to drive such a pump. Secondly, the present invention is considerably less complicated than external blood warming systems. Known systems circulate the blood over a relatively lengthy path from the patient, through the warming element, and back into the patient. It is expected that more heat is lost over this lengthy path than will be lost in any device according to the present invention.

Thus, the power required by external blood circulation and warming systems of the type previously known can be used as a rough estimate of the likely upper limit for power required by a system according to the present invention. It is most likely that such a system will best be equipped with a power supply having a capacity somewhere between the two rough estimates described above. It is therefore contemplated that a suitable power supply will be capable of providing peak power somewhere in the range between 100 and 1500 watts, probably being in the range between 300 and 1000 watts. The ranges specified are an estimate of suitable peak power capability. The power supply will most commonly be thermostatically controlled in response to a temperature sensor in the body of the catheter. The actual effective power transmitted to the patient will therefore typically be much less than the peak power capacity of the system power supply.

With respect to a catheter for cooling, the temperature and power constraints are not as limiting as is the case in a catheter for warming blood. Care should merely be taken to avoid freezing the blood or inducing shock to the patient from too rapid cooling.

Blood is essentially water containing a number of suspended and dissolved substances. As such, its freezing point is somewhat below 0° C. However, a catheter adapted to cool blood in a hyperthermic patient or to induce an artificial hypothermia will usually not be operated at temperatures that low. It is presently contemplated that the external surface of such a catheter may be held in the range between about 20° C. and 24° C., although the actual temperature could vary between about 0° C. and the patient's current body temperature (somewhat in excess of 37° C.).

Various embodiments of apparatus suitable for practicing the methods of the present invention have been described.

Other embodiments and modifications will occur to those skilled in the art. For example, various means for heat transfer, e.g., resistance, including radio frequency, heating; laser energy; pumped fluids; etc., may be combined with various means for increasing the effective heat transfer surface area, e.g., balloons, fins, ribs, etc., to optimize the function of a device according to the present invention. Also, a temperature sensor will typically be used although for ease of illustration such a sensor is not depicted in all of the embodiments described. Furthermore, although most of the figures depict embodiments in which only a limited portion of the catheter is temperature controlled, no reason exists to prevent warming or cooling substantially the whole length of the catheter.

Broadly stated, the present invention provides a method for modifying a patient's body temperature by controlling the temperature of a catheter inserted into a blood vessel of the patient. Although several illustrative examples of means for practicing the invention are described above, these examples are by no means exhaustive of all possible means for practicing the invention. The scope of the invention should therefore be determined with reference to the appended claims, along with the full range of equivalents to which those claims are entitled.

What is claimed is:

1. A method for lowering the core body temperature of a patient, said method comprising the steps of:
   A. monitoring the patient's core body temperature;
   B selecting a desired core body temperature that is lower than the patient's current core body temperature;
   C. providing a heat exchange catheter which is insertable into the patient's vasculature, said heat exchange catheter comprising an elongate, flexible catheter body and a heat exchanger which occupies less than the entirety of the catheter body, said heat exchanger comprising a balloon through which a cooled fluid is circulated;
   D. inserting the heat exchange catheter into the patient's vasculature such that the heat exchanger is positioned within a blood vessel through which blood is flowing;
   E. circulating cooled fluid through said balloon to lower the monitored core body temperature to approximately the desired core body temperature.

2. A method according to claim 1 wherein the patient's core body temperature is lowered below 37 degrees C.

3. A method according to claim 1 wherein the patient's core body temperature is temporarily lowered to a hypothermic temperature.

4. A method according to claim 3 wherein the patient's core body temperature is temporarily lowered to a hypothermic temperature to reduce the patient's need for oxygen.

5. A method according to claim 1 wherein the method is carried out to cool a patient who is hyperthermic.

6. A method according to claim 1 wherein the catheter body comprises an inflow lumen through which fluid flows into the heat exchanger and an outflow lumen through which fluid flows out of the heat exchanger and where Step E comprises causing cooled fluid to flow into the heat exchanger through the inflow lumen and out of the heat exchanger through the outflow lumen.

7. A method according to claim 1 further comprising the step of:
   removing the catheter from the patient's vasculature.

8. A method for altering the body temperature of a patient, said method comprising the step of:
   A. providing a heat exchange catheter which is insertable into the patient's vasculature, said heat exchange catheter comprising an elongate, flexible catheter body having a heat exchanger which comprises a balloon through which the fluid is circulated and which occupies less than the entirety of the catheter body, said heat exchanger being operative to exchange heat with the patient's blood;
   B. inserting the heat exchange catheter into the patient's vasculature such that the heat exchanger is positioned within a blood vessel through which blood is flowing;
   C. positioning a temperature measuring device in the patient's body and using said temperature measuring device to measure the patient's core body temperature;
   D. selecting a desired core body temperature that is different form the currently measured core body temperature; and
   E. controlling the heat exchanger by circulating said fluid through said balloon to cause the patients blood to be warmed or cooled sufficiently to change the measured core body temperature to approximately the desired core body temperature.

9. A method according to claim 8 wherein the patient's body temperature is lowered.

10. A method according to claim 8 wherein the patient's body temperature is lowered below 37 degrees C.

11. A method according to claim 8 wherein the patients body temperature is raised.

12. A method according to claim 8 wherein the patient's body temperature is temporarily lowered to a hypothermic temperature.

13. A method according to claim 12 wherein the patient's body temperature is temporarily lowered to a hypothermic temperature to reduce the patient's need for oxygen.

14. A method according to claim 8 wherein the method is carried out to warm a patient who is hypothermic.

15. A method according to claim 8 wherein the method is carried out to cool a patient who is hyperthermic.

16. A method according to claim 8 wherein the catheter body comprises an inflow lumen through which fluid flows into the heat exchanger and an outflow lumen through which fluid flows out of the heat exchanger and where Step E comprises causing heated or cooled fluid to flow into the heat exchanger through the inflow lumen and out of the heat exchanger through the outflow lumen.

17. A method according to claim 8 further comprising the step of:
   F. removing the catheter from the patient's vasculature.

18. A method according to claim 8 wherein Step D comprises monitoring the temperature of the distal end of the catheter.

19. A method for altering the body temperature of a patient, said method comprising the step of:
   A. providing a heat exchange catheter which is insertable into the patient's vasculature, said heat exchange catheter comprising an elongate, flexible catheter body having a heat exchanger which occupies less than the entirety of the catheter body, said heat exchanger being operative to exchange heat with the patient's blood;
   B. inserting the heat exchange catheter into the patient's vasculature such that the heat exchanger is positioned within a blood vessel through which blood is flowing;
   C. positioning a temperature measuring device in the patients body and using said temperature measuring device to measure the patient's core body temperature;
   D. selecting a desired core body temperature that is different form the currently measured core body temperature; and
   E. controlling the heat exchanger to cause the patient's blood to be warmed or cooled sufficiently to change the measured core body temperature to approximately the desired core body temperature;

wherein:

i) the heat exchange catheter includes a power source;

ii) Step D comprises measuring the surface temperature of the catheter body; and iii) Step E comprises controlling the delivery of power from the power source to the heat exchanger according to the measured temperature of the catheter.

20. A method according to claim 19 wherein the patient's body temperature is lowered.

21. A method according to claim 19 wherein the patient's body temperature is lowered below 37 degrees C.

22. A method according to claim 19 wherein the patient's body temperature is raised.

23. A method according to claim 19 wherein the patient's body temperature is temporarily lowered to a hypothermic temperature.

24. A method according to claim 23 wherein the patient's body temperature is temporarily lowered to a hypothermic temperature to reduce the patient's need for oxygen.

25. A method according to claim 19 wherein the method is carried out to warm a patient who is hypothermic.

26. A method according to claim 19 wherein the method is carried out to cool a patient who is hyperthermic.

27. A method according to claim 19 wherein the heat exchanger is constructed such that heated or cooled fluid is circulated through the heat exchanger and wherein Step E comprises circulating heated or cooled fluid through said heat exchanger.

28. A method according to claim 27 wherein the heat exchanger comprises a balloon through which the fluid is circulated and wherein Step E comprises circulating said fluid through said balloon.

29. A method according to claim 19 wherein the catheter body comprises an inflow lumen through which fluid flows into the heat exchanger and an outflow lumen through which fluid flows out of the heat exchanger and where Step E comprises causing heated or cooled fluid to flow into the heat exchanger through the inflow lumen and out of the heat exchanger through the outflow lumen.

30. A method according to claim 19 further comprising the step of:

F. removing the catheter from the patient's vasculature.

31. A method according to claim 19 wherein Step D comprises monitoring the surface temperature of the catheter body at the distal end of the catheter.

* * * * *